United States Patent [19]

Schaffner et al.

[11] Patent Number: 4,864,037
[45] Date of Patent: Sep. 5, 1989

[54] OPTICALLY PURE 1,3-DIOXENONES, METHODS FOR PREPARING SAME AND USE THEREOF

[75] Inventors: Kurt Schaffner; Martin Demuth, both of Mülheim, Fed. Rep. of Germany

[73] Assignee: Studiengesellschaft Kohle mbH, Mulheiman, Fed. Rep. of Germany

[21] Appl. No.: 76,412

[22] Filed: Jul. 21, 1987

[30] Foreign Application Priority Data

Jul. 23, 1986 [DE] Fed. Rep. of Germany ....... 3624912

[51] Int. Cl.$^4$ .................. C07D 319/06; C07D 319/00
[52] U.S. Cl. ..................................... 549/274; 568/839
[58] Field of Search ......................... 549/274; 568/839

[56] References Cited

U.S. PATENT DOCUMENTS 4,582,913  4/1986  Clemens ............................. 549/274
4,612,379  9/1986  Kaneko et al. ..................... 549/274

FOREIGN PATENT DOCUMENTS 0254239  1/1988  European Pat. Off. ............ 549/274
61-022077  1/1986  Japan ................................. 549/274

OTHER PUBLICATIONS

Billups et al., "A Synthesis of (±)-Grandisol", Journal of the American Chemical Society, Vol. 95, No. 10, (1973), pp. 3438–3439.

Ayer et al., "The Transformation of Carvone Into Racemic Grandisol", Canadian Journal of Chemistry, Vol. 52, No. 8, (1974), pp. 1352–1360.

Y. Oikawa et al., "Meldrum's Acid in Organic Syntheses . . . ", J. Org. Chem., vol. 43, (No. 10, 1978) pp. 2087–2088.

Primary Examiner—William R. Dixon, Jr.
Assistant Examiner—Anthony J. Green
Attorney, Agent, or Firm—Sprung Horn Kramer & Woods

[57] ABSTRACT

Disclosed are new 1,3-dioxenones having the formulae

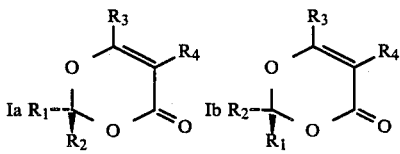

in an optically pure state, a process for preparing same and the use thereof.

4 Claims, No Drawings

OPTICALLY PURE 1,3-DIOXENONES, METHODS FOR PREPARING SAME AND USE THEREOF

The present invention relates to optically pure 1,3-dioxenones having the formulae Ia and Ib and the preparation thereof by acetalization of an acetoacetic acid derivative with an optically active carbonyl component and separation of the product mixture by chromatography or distillation or by crystallization.

Y. Oikawa, K. Sugano, O. Yonemitsu, J. Org. Chem. 43, 2087 (1978) already described the synthesis of the racemic mixture of a 1,3-dioxenone of the formula I (Ia=Ib; $R_1=R_2=CH_3$) starting from a 1,3-dioxanedione. An accumulation or synthesis in a pure state of optically active 1,3-dioxenones of the formulae Ia and/or Ib so far has not been described.

Thus, the invention relates to 1,3-dioxenones of the formulae Ia and Ib in their optically active forms and at the same time in an optically pure state

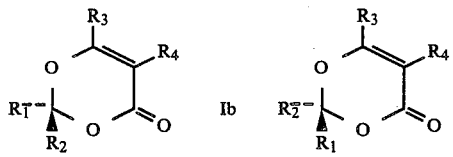

wherein $R_1$, $R_2$, $R_3$ and $R_4$ may be H, $C_1$-$C_8$-alkyl, $C_1$-$C_8$-alkoxyl, and hydroxylated and/or carbonylated $C_1$-$C_8$-alkyl groups which may contain one or more double bond(s), may further be aryl groups, Cl, Br, F and CN as well as COOH and/or the esters thereof and —C(=O)—R [wherein R may be H, $C_1$-$C_8$-alkyl, $C_1$-$C_8$-alkoxyl, and a hydroxylated and/or carbonylated $C_1$-$C_8$-alkyl group which may contain one or more double bond(s) and/or triple bond(s) and or aryl groups]. $R_1$ and $R_2$ may also represent a ring of the size $C_2$-$C_{12}$ which in turn may also be $C_1$-$C_8$-alkylated, alkoxylated, hydroxylated and/or carbonylated and/or arylated. Said ring may also contain one or more double bond(s) and/or triple bond(s). In addition to ring carbon atoms there may also be present hetero atoms such as nitrogen, oxygen, sulfur, boron. Furthermore, $R_1$ must always be different from $R_2$. $R_1$ and $R_2$ may be parts of a common ring which ring should bear at least one center of chirality.

The invention further relates to a method for preparing optically pure 1,3-dioxenones having the formulae Ia and Ib wherein $R_1$, $R_2$, $R_3$ and $R_4$ are defined as above, which method is characterized in that a cyclic or acyclic carbonyl compound having the formula III

which is optically active and wherein $R_1$ and $R_2$ are defined as above are acetalized with an acetoacetic acid derivative having the formula IV

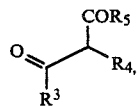

wherein $R_3$ and $R_4$ are defined as above, and the obtained condensation products, viz. the 1,3-dioxenones of the formulae Ia and Ib, are separated by chromatography and/or distillation and/or preferably by crystallization. $R_5$ is to be selected so that —$COR_5$ in the formula IV is a conventional carboxylic acid derivative or the acid itself ($R_5$=OH).

The $C_1$-$C_8$-alkyl, $C_1$-$C_8$-alkoxyl, and hydroxylated and/or carbonylated $C_1$-$C_8$-alkyl groups may include straight-chain and branched alkyl groups. $R_1$ and $R_2$ especially may also be parts of a common ring.

Thus, examples for the $C_1$-$C_8$ groups in $R_1$ to $R_4$ include: H, methyl, ethyl, i- and n-propyl, n-but-1-yl, n-but-2-yl, isobutyl, t-butyl; among the $C_4$-$C_8$-alkyl, alkoxyl and hydroxylated and carbonylated alkyl groups, the n-alkyl groups as well as the 2- and 3-methylalkyl groups are preferred. The double bonds, triple bonds, OH groups and C=O groups in the $C_2$-$C_8$-alkyl, alkoxyl and hydroxylated and carbonylated alkyl groups are preferably in the 1-, 2- and 3-positions. The aryl groups in $R_1$ to $R_4$ are preferred to be substituted phenyl, naphthyl or anthracyl nuclei which may also bear hetero atoms, preferably nitrogen (for example, pyridine derivatives). In the case that $R_1$ and $R_2$ are parts of a common ring, said ring may be derived from (+)-camphor (carbonyl component III=camphor) or preferably from (−)-menthone carbonyl component III=menthone). Examples for $R_5$ include OH, Cl, methoxy, i- and n-propoxy, t-butoxy, phenoxy and acetoyl.

The object of the present invention has been attained by reacting an optically carbonyl component of the formula III with an acetoacetic acid derivative of the formula IV to form Ia and Ib (acetalization) and separating Ia and Ib from each other by chromatography, distillation or, preferably, by crystallization. It was surprisingly found that both forms, Ia and Ib, are formed and can be readily separated by crystallization and chromatography to form the pure compounds. As the carbonyl component III, (−)-menthone was found to be particularly suitable.

Furthermore it was suprisingly found that the formation ratio of Ia and Ib in the course of the acetalization may be varied by the selection of the acid to be employed and the reaction temperature. Thus, by using sulfuric acid, the Ia/Ib ratio obtained is 6:1 at a temperature of −5° C. and 1:1 at a temperature of 10° C. By using p-toluenesulfonic acid the Ia/Ib ratio obtained is 4:1 at a temperature of −5° C. The acetalization of III+IV to form Ia+Ib may be effected in the presence as well as in the absence of a solvent.

1,3-Dioxenones are starting compounds for the syntheses of (+)- and (−) -Grandisols (pheromones) [M. Demuth, A. Palomer, H.-D. Sluma, A. K. Dey, C. Kröger and Y.-H. Tsay, Angew. Chem. Int. Ed. Engl. 25, 1117 (1986)].

The invention is further illustrated by the following examples.

EXAMPLES 1 and 2

III = (−)-menthone =

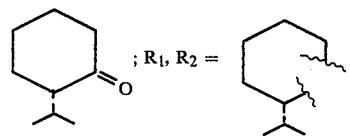

$R_3 = CH_3$; $R_4 = H$; $R_5 = O\text{---}\underline{t}\text{-butyl}$.

EXAMPLE 1

31 g of (—)-menthone were mixed with 32 g of (IV) ($R_3=CH_3$; $R_4=H$; $R_5=O$-t-butyl; t-butyl acetoacetate) and 68 g of acetic anhydride. 10 ml of sulfuric acid were dropwise added at $-5°$ C., and the mixture was stirred for 48 h. Then the mixture was added to 1 liter of a stirred cold 10% aqueous sodium carbonate solution, and the resulting mixture was extracted with ether. The organic phase contained Ia and Ib in a ratio of 6:1. Purification of the residue on silica gel (solvent: n-hexane+ethyl acetate-9:1) yielded 7 g of Ia ($R_1$, $R_2$=parts of the menthone backbone; $R_3=CH_3$, $R_4=H$) and 1.2 g of Ib ($R_1$, $R_2$=parts of the menthone backbone; $R_3=CH_3$, $R_4=H$). Total yield: 34%.

EXAMPLE 2

60 g of (—)-menthone were mixed with 61 g of (IV) ($R_3=CH_3$; $R_4=H$; $R_5=O$-t-butyl; t-butyl acetoacetate) and 120 ml of acetic anhydride. 40 ml of sulfuric acid were dropwise added at $-10°$ C., and the mixture was stirred for 2 h at room temperature. Then the mixture was extracted two times with 500 ml portions of aqueous sodium hydrogencarbonate solution (10%) and with ether. The organic phase contained Ia and Ib in a ratio of 1:1. The organic phase was concentrated by evaporation, and residue was taken up in n-hexane. 7.5 g of Ib ($R_1$, $R_2$=parts of the menthone backbone; $R_3=CH_3$, $R_4=H$) crystallized. The filtrate contained 10 g of Ia (contaminated by a small proportion of Ib) which was subsequently purified on silica gel (solvent: n-hexane+ethyl acetate-9:1). Thereby, 8 g of purest Ia ($R_1$, $R_2$=parts of the menthone backbone; $R_3=CH_3$, $R_4=H$) were eluated.

Spectroscopic Data (EXAMPLES 1 and 2)
IR: $\gamma=1710$, 1225, 1180, 1140, 1075 cm$^{-1}$
MS: m/z 238 (M+), 196, 154, 139, 112, 69, 55, 41.
$^1$H-NMR: $\delta=5.12$ (s, 1H), 2.56 (ddd, J=2.5, 3.5, 13.5 Hz, 1H), 2.17 (dh, J=2.5, 7 Hz, 1H), 1.94 (s, 3H), 1.42–1.80 (m, 6H), 0.97 (t, J=13 Hz, 1H), 0.91 (d, J=7 Hz, 3H), 0.87 (d, J=7 Hz, 3H), 0.84 (d, J=6 Hz, 3H).
$^{13}$C-NMR: $\delta=168.6$, 161.0, 109.7, 93.1, 49.3, 40.9, 34.0, 28.5, 25.5, 23.1, 22.2, 21.5, 20.0, 18.5. $[\alpha]_D=-27.4°$ (c=0.48, chloroform).
Ib (EXAMPLES 1 and 2)
Melting point: 49° C.
IR: $\gamma=1710$, 1630, 1275, 1075 cm$^{-1}$.
MS: m/z 238 (M+).
$^1$H-NMR $\delta=5.16$ (s, 1H), 2.57 (ddd, J=1, 2, 14 Hz, 1H), 2.29 (gh, J=1, 7 Hz, 1H), 1.95 (s, 3H), 1.74 (dm, J=13 Hz, 1H), 1.65 (m, 1H), 1.44–1.56 (m, 4H), 1.05 (t, J=13 Hz, 1H), 0.9 (d, J=7 Hz, 3H), 0.85 (d, J=7 Hz, 3H), 0.83 (d, J=7 Hz, 3H).
$^{13}$C-NMR: $\delta=168.0$, 161.5, 109.5, 93.6, 49.1, 40.3, 33.8, 29.6, 25.1, 23.0, 21.7, 21.5, 20.0, 18.1.
$[\alpha]_D=-22.5°$ (c=0.4, chloroform).

EXAMPLE 3

III=(—)-menthone; $R_1$ and $R_2$ see Examples 1 and 2; $R_3=CH_3$; $R_4=COO$-t-butyl; $R_5=O$-t-butyl.

EXAMPLE 3

60 g of (—)-menthone were mixed with 70 g of (IV) ($R_3=CH_3$; $R_4=R_5=O$-t-butyl) and 120 ml of acetic anhydride. 40 ml of sulfuric acid were dropwise added at $-10°$ C., and the mixture was stirred for 10 h. The procedure was continued according to Example 1, and Ia ($R_1$, $R_2$=parts of the menthone backbone; $R_3=CH_3$, $R_4=COO$-t-butyl) and Ib ($R_1$, $R_2$=parts of the menthone backbone; $R_3=CH_3$, $R_4=COO$-t-butyl) were obtained at a ratio of 6:1 in comparable yields.

Spectroscopic Data

Ia (EXAMPLE 3)
IR: $\gamma=1710$, 1695, 1630, 1225, 1180, 1140, 1065 cm$^{-1}$.
MS: m/z 338 (M+).
$^1$H-NMR: $\delta=2.5$ (ddd, J=3, 3.5, 13.5 Hz, 1H), 2.17 (dh, J=3, 7.5 Hz, 1H), 1.94 (s, 3H), 1.4–1.85 (m, 6H), 0.99 (t, J=13 Hz, 1H), 0.9 (d, J=7.5 Hz, 3H), 0.85 (d, J=7.5 Hz, 3H), 0.82 (d, J=6 Hz, 3H), 0.78 (s, 9H).
$[\alpha]_D=-37.4°$ (c=0.44, chloroform).
Ib (EXAMPLE 3)
IR: $\gamma=1710$, 1700, 1625, 1270, 1095 cm$^{-1}$.
MS: m/z 338 (M+).
$^1$H-NMR: $\gamma=2.55$ (ddd, J=1, 2, 12 Hz, 1H), 2.3 (dh, J=1, 7.5 Hz, 1H), 1.92 (s, 3H), 1.75 (dm, J=12 Hz, 1H), 1.65 (m, 1H), 1.5–1.65 (m, 4H), 1.0 (t, J=12 Hz, 1H), 0.9 (d, J=7.5 Hz, 3H), 0.83 (d, J=7.5 Hz, 3H), 0.81 (d, J=7.5 Hz, 3H), 0.78 (s, 9H).

EXAMPLE 4

III = (—)-8-phenylmenthone;

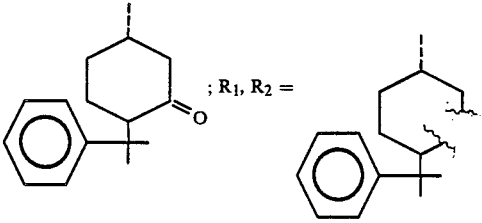

$R_3 = CH_3$; $R_4 = H$; $R_5 = O\text{---}\underline{t}\text{-butyl}$.

EXAMPLE 4

45 g of (—)-8-phenylmenthone were mixed with 30 g of (IV) ($R_3=CH_3$; $R_4=H$, $R_5=O$-t-butyl; t-butyl acetoacetate), 120 ml of acetic anhydride and 200 ml of dibutylether. 15 ml of sulfuric acid were dropwise added at $-10°$ C., and the mixture was stirred for 4 h at room temperature. The procedure was continued according to Example 2, and Ia ($R_1$, $R_2$=parts of the 8-phenylmenthone backbone; $R_3=CH_3$, $R_4=H$) and Ib ($R_1$, $R_2$=parts of the 8-phenylmenthone backbone; $R_3=CH_3$, $R_4=H$) were obtained at a ratio of 1:1 in comparable yields.

EXAMPLE 5

III = (+)-2,3-O—isopropylidene-glycerinaldehyde =

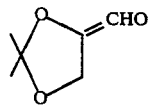

$R_1 = H; R_2 =$ or $R_2 = H; R_1 =$

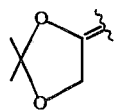

$R_3 = CH_2CH_3; R_4 = Cl; R_5 = OCH_3.$

EXAMPLE 5

27 g of (+)-2,3-O-isopropylidene-glycerinaldehyde together with 28 g of (IV) ($R_3=CH_2CH_3$; $R_4=Cl$, $R_5=OCH_3$) were dissolved in 200 ml of dichloromethane. 10 g of p-toluenesulfonic acid were added at $-30°$ C., and the mixture was stirred at that temperature for 15 h. The procedure was continued according to Example 1, and Ia ($R_1=H$, $R_2=$parts of the 2,3-O-isopropylidene-glycerinaldehyde backbone; $R_3=CH_2CH_3$, $R_4=Cl$) and Ib ($R_2=H$, $R_1=$parts of the 2,3-O-isopropylidene-glycerinaldehyde backbone; $R_3=CH_2CH_3$, $R_4=Cl$) were obtained at a ratio of 4:1 in comparable yields.

EXAMPLE 6

III=(+)-2,3-O-isopropylidene-glycerinaldehyde; $R_1$ and $R_2$ see Example 5. $R_3=CH_2CH_3$; $R_4=(C=O)-C=C-C_4H_9$, $R_5=H$.

EXAMPLE 6

54 g of (+)-2,3-O-isopropylidene-glycerinaldehyde together with 35 g of (IV) ($R_3=CH_2CH_3$; $R_4=(C=O)-C=C-C_4H_9$, $R_5=H$) were dissolved in 500 ml of tetrahydrofurane. 15 g of p-toluenesulfonic acid were added at $-5°$ C., and the mixture was stirred at that temperature for 7 h. The procedure was continued according to Example 1, and Ia ($R_1=H$, $R_2=$parts of the 2,3-O-isopropylidene-glycerinaldehyde backbone; $R_3=CH_2CH_3$, $R_4=(C=O)-C=C-C_4H_9$, $R_5=H$) and Ib ($R_2=H$, $R_1=$parts of the 2,3-O-isopropylidene-glycerinaldehyde backbone; $R_3=CH_2CH_3$, $R_4=(C=O)-C=C-C_4H_9$, $R_5=H$) were obtained at a ratio of 4:1 in comparable yields.

EXAMPLE 7

III = pulegone =

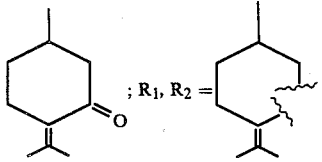

$R_3 = CH_2CH_2(-2\text{-pyridyl})$ or $CH_2CH_2(3\text{-indolyl})$,
$R_4 = CH_2-C(CH_3)=CH_2$; $R_5 = O(CO)CH_3$.

EXAMPLE 7

50 g of (+)-pulegone together with 105 g of (IV) ($R_3=CH_2CH_2(-2\text{-pyridyl})$ or $CH_2CH_2(3\text{-indolyl})$, $R_4=CH_2-C(CH_3)=CH_2$; $R_5=O(CO)CH_3$) were dissolved in 100 ml of acetic anhydride and 500 ml of tetrahydrofurane. 20 g of hydrochloric acid were added at $-20°$ C., and the mixture was stirred at that temperature for 15 h. The procedure was continued according to Example 1, and Ia {$R_1$, $R_2=$parts of the pulegone backbone; $R_3=CH_2CH_2(-2\text{-pyridyl})$ or $CH_2CH_2(3\text{-indolyl})$, $R_4=CH_2-C(CH_3)=CH_2$} and Ib {$R_1$, $R_2=$parts of the pulegone backbone; $R_3=CH_2CH_2(-2\text{-pyridyl})$ or $CH_2=CH_2(3\text{-indolyl})$, $R_4=CH_2-C(CH_3)=CH_2$} were obtained at a ratio of 5.5:1 in comparable yields.

We claim:

1. An optically pure, 1,3-dioxenone of the formula Ia or Ib

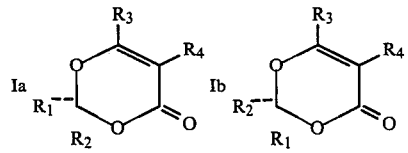

wherein
$R^1$ and $R^2$ are different and
$R^1$, $R^2$, $R^3$ and $R^4$ are each independently selected from the group consisting of H, $C_1$-$C_8$-alkyl, $C_1$-$C_8$-alkoxy, hydroxy-$C_1$-$C_8$-alkyl, carboxy-$C_1$-$C_8$-alkyl, $C_1$-$C_8$-alkenyl, $C_1$-$C_8$-alkenoxy, hydroxy-$C_1$-$C_8$-alkenyl, carboxy-$C_1$-$C_8$-alkenyl or aryl, Cl, Br, F, CN, COOH, COO-alkyl or —C(=)—R substitution products thereof, and
R is H, $C_1$-$C_8$-alkyl, $C_1$-$C_8$-alkoxy, hydroxy-$C_1$-$C_8$-alkyl, carboxy-$C_1$-$C_8$-alkyl, $C_1$-$C_8$-alkenyl, $C_1$-$C_8$-alkenoxy, hydroxy-$C_1$-$C_8$-alkenyl, carboxy-$C_1$-$C_8$-alkenyl or aryl.

2. A process for the preparation of an optically pure 1,3-dioxenone of the formula Ia or Ib

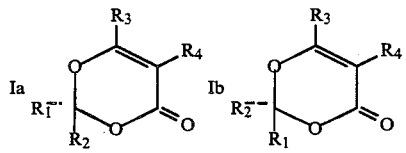

wherein
$R^1$ and $R^2$ are differnet and
$R^1$, $R^2$, $R^3$ and $R^4$ are each independently selected from the group consisting of H, $C_1$-$C_8$-alkyl, $C_1$-$C_8$-alkoxy, hydroxy-$C_1$-$C_8$-alkyl, carboxy-$C_1$-$C_8$-alkyl, $C_1$-$C_8$-alkenyl, $C_1$-$C_8$-alkenoxy, hydroxy-$C_1$-$C_8$-alkenyl, carboxy-$C_1$-$C_8$-alkenyl or aryl, Cl, Br, F, CN, COOH, COO-alkyl or —C(=O)—R substitution products thereof, and
R is H, $C_1$-$C_8$-alkyl, $C_1$-$C_8$-alkoxy, hydroxy-$C_1$-$C_8$-alkyl, carboxy-$C_1$-$C_8$-alkyl, $C_1$-$C_8$-alkenyl, $C_1$-$C_8$-alkenoxy, hydroxy-$C_1$-$C_8$-alkenyl, carboxy-$C_1$-$C_8$-alkenyl or aryl, which comprises reacting an optically active compound of the formula

with an acetoacetic acid derivative of the formula

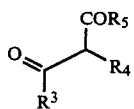

(IV)

in which $R_5$ is OH or alkyl, thereby to form a mixture of compounds Ia and Ib, and separating Ia and Ib by chromatography, distillation or crystallization.

3. The process of according to claim 2, wherein (III) is (−)-menthone.

4. In the synthesis of a Grandisol from a 1,3-dioxenone, the improvement which comprises employing an optically pure 1,3-dioxenone according to claim 1, whereby the resulting Grandisol is optically pure.

* * * * *

UNITED STATES PATENT AND TRADEMARK OFFICE
CERTIFICATE OF CORRECTION

PATENT NO. : 4,864,037
DATED : September 5, 1989
INVENTOR(S) : Kurt Schaffner, et al It is certified that error appears in the above-identified patent and that said Letters Patent is hereby corrected as shown below:

Col. 6, lines 11-18,   Delete formulas Ia and Ib and substitute:

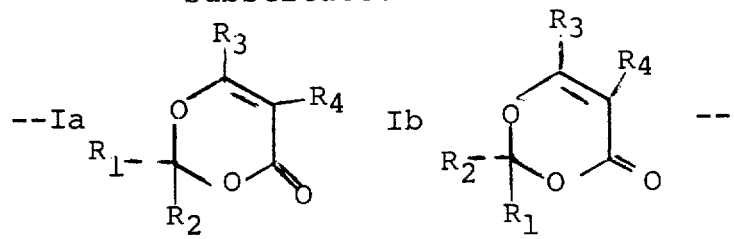

Col. 6, line 29   Delete "=)-R" and substitute -- =O)-R --

Col. 6, line 40   Correct spelling of --different--

Signed and Sealed this

Twenty-seventh Day of November, 1990

Attest:

HARRY F. MANBECK, JR.

Attesting Officer   Commissioner of Patents and Trademarks

UNITED STATES PATENT AND TRADEMARK OFFICE
CERTIFICATE OF CORRECTION

PATENT NO. : 4,864,037

DATED : September 5, 1989

INVENTOR(S) : Kurt Schaffner, et al

It is certified that error appears in the above-identified patent and that said Letters Patent is hereby corrected as shown below:

Col. 2, line 63-68    Delete formulas and substitute:

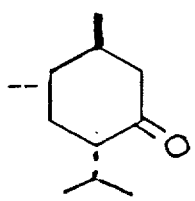 ; $R_1, R_2 =$ 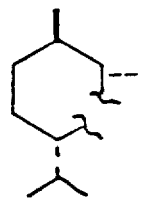

Col. 4, line 65-68    Delete formula and substitute:

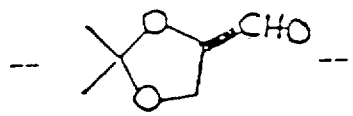

UNITED STATES PATENT AND TRADEMARK OFFICE
CERTIFICATE OF CORRECTION

PATENT NO. : 4,864,037

DATED : September 5, 1989

INVENTOR(S) : Kurt Schaffner, et al

It is certified that error appears in the above-identified patent and that said Letters Patent is hereby corrected as shown below:

Col. 5, line 5-8        Delete formula and substitute:

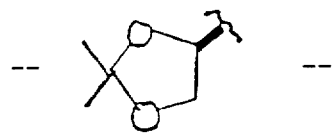

Signed and Sealed this

Ninth Day of April, 1991

*Attest:*

HARRY F. MANBECK, JR.

*Attesting Officer*    *Commissioner of Patents and Trademarks*